United States Patent [19]

Knorr

[11] Patent Number: 4,707,602

[45] Date of Patent: Nov. 17, 1987

[54] FOURIER TRANSFORM TIME OF FLIGHT MASS SPECTROMETER

[75] Inventor: Fritz J. Knorr, Mountain View, Calif.

[73] Assignee: Surface Science Laboratories, Inc., Mountain View, Calif.

[21] Appl. No.: 801,207

[22] Filed: Nov. 25, 1985

Related U.S. Application Data

[63] Continuation-in-part of Ser. No. 724,514, Apr. 8, 1985, Pat. No. 4,633,083.

[51] Int. Cl.$^4$ ............................................. B01D 59/44
[52] U.S. Cl. ................................. 250/282; 250/281; 250/287; 364/498
[58] Field of Search ............... 250/281, 282, 283, 286, 250/287; 364/498

[56] References Cited

U.S. PATENT DOCUMENTS

| | | | |
|---|---|---|---|
| 3,553,452 | 1/1971 | Tierman | 250/287 |
| 3,629,574 | 12/1971 | Carroll et al. | 250/287 |
| 3,920,978 | 2/1974 | Schmitt | 364/726 |
| 3,989,938 | 11/1976 | Auth | 364/498 |
| 4,390,784 | 6/1983 | Browning | 250/287 |
| 4,514,822 | 4/1985 | Schneider | 364/498 |
| 4,590,574 | 5/1986 | Edmonds et al. | 364/498 |

OTHER PUBLICATIONS

"Fourier Transform Ion Mobility Spectrometry", Knorr et al., Anal. Chem., vol. 57, No. 2, 2-85, pp. 402-406.

Primary Examiner—Bruce C. Anderson
Attorney, Agent, or Firm—Harry E. Aine

[57] ABSTRACT

A time of flight mass spectrometer includes means for gating the flow of ions from the source to the detector with a modulation function, the frequency of which is swept. The detected ion current is obtained as a function of the ion current modulation frequency to derive an ion mass interferogram output in the frequency domain. The interferogram output is Fourier transformed from the frequency domain to the time domain to obtain a time of flight mass spectrum output in the time domain. The Fourier transform time of flight mass spectrometer provides increased duty cycle and signal-to-noise ratio for a given scan time.

8 Claims, 4 Drawing Figures

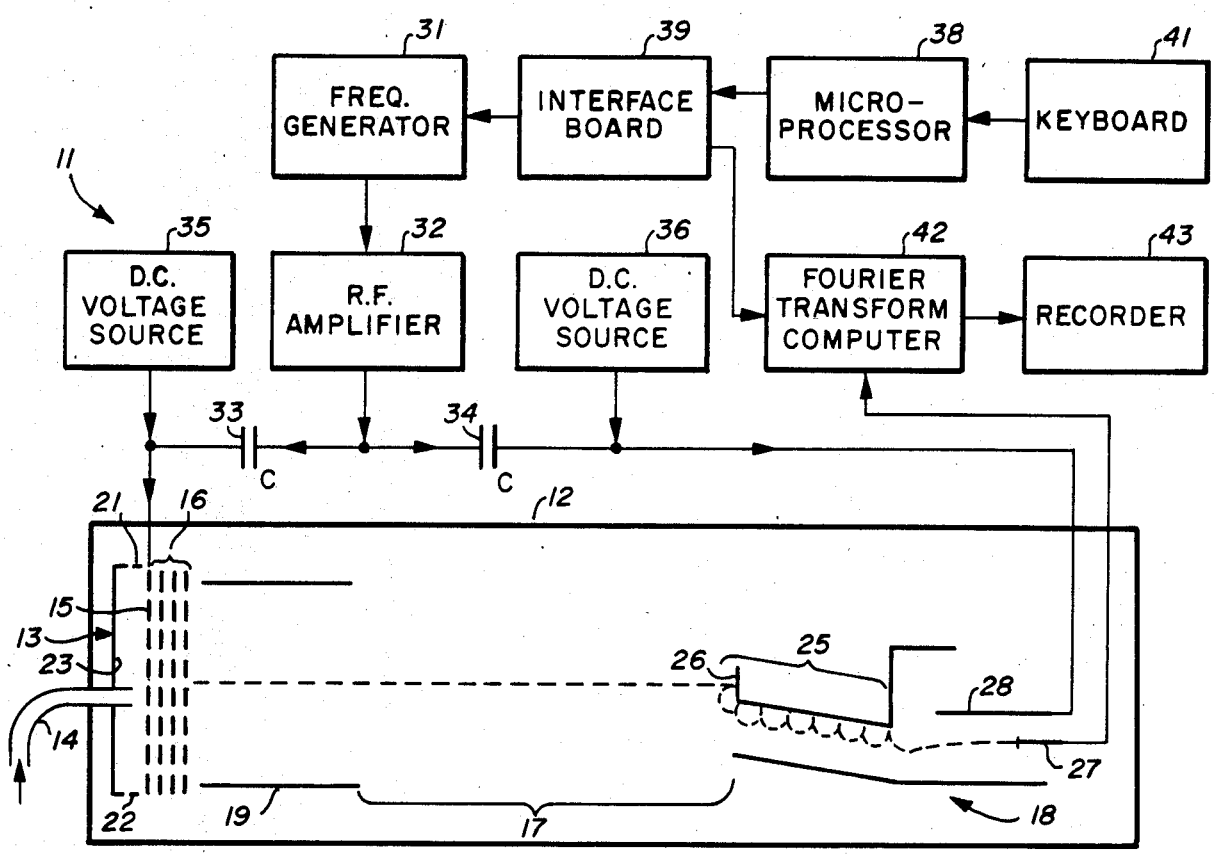
Fig_1
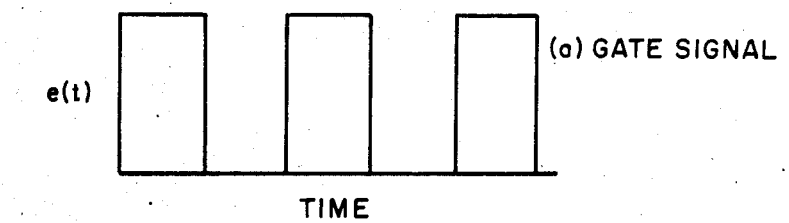
(a) GATE SIGNAL
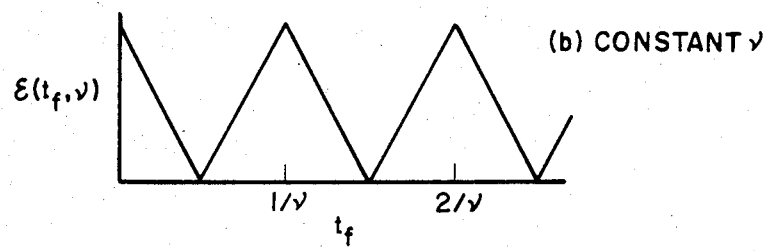
(b) CONSTANT $\nu$
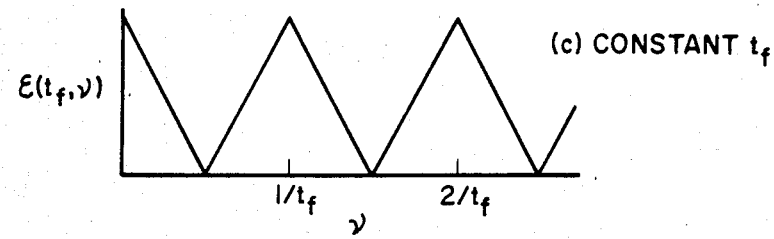
(c) CONSTANT $t_f$
Fig_2

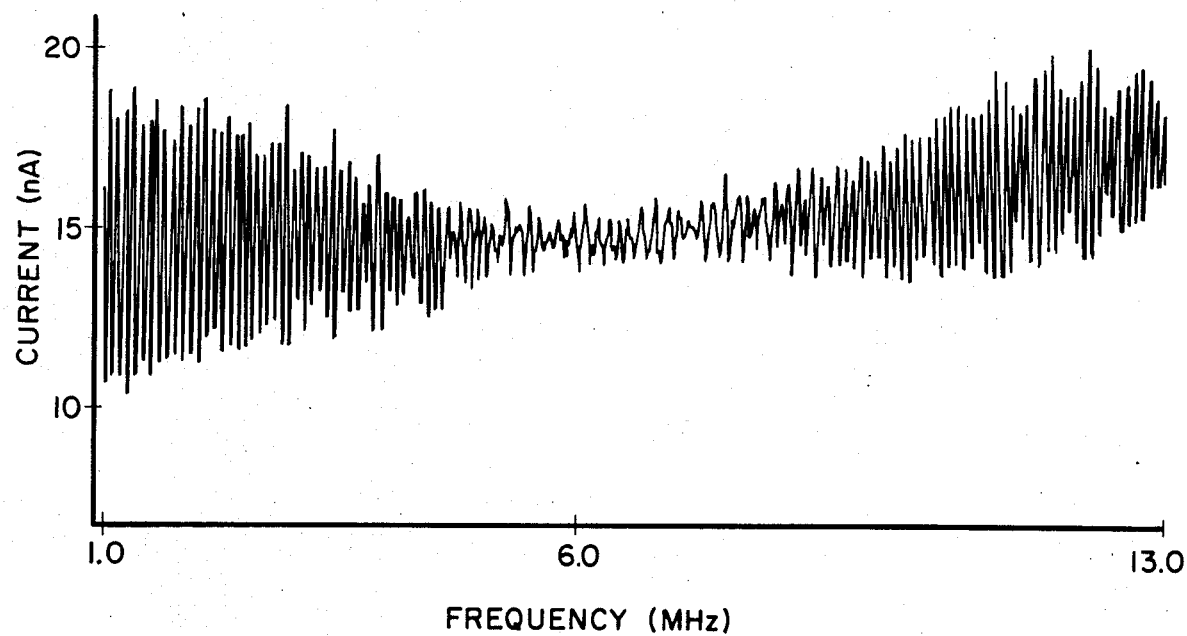
Fig_3
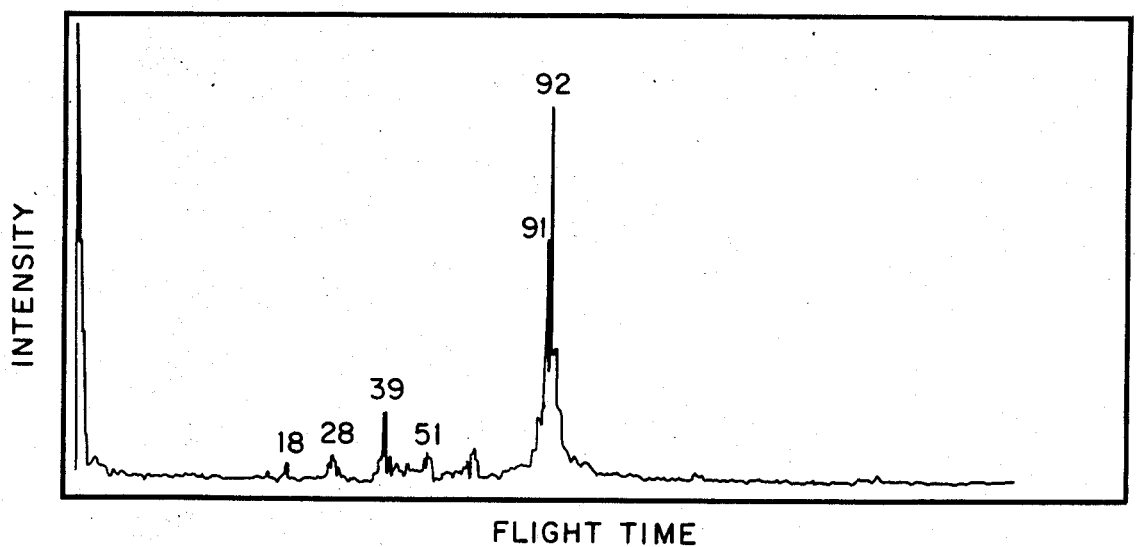
Fig_4

FOURIER TRANSFORM TIME OF FLIGHT MASS SPECTROMETER

RELATED CASES

The present invention is a continuation-in-part invention of co-pending U.S. Ser. No. 724,514 filed Apr. 8, 1985 U.S. Pat. No. 4,633,083.

BACKGROUND OF THE INVENTION

The present invention relates in general to time of flight mass spectrometers, and, more particularly, to such a spectrometer operated in such a manner as to derive an output in the frequency domain which is thence Fourier transformed to the time domain to obtain a conventional time of flight mass spectrometer output.

DESCRIPTION OF THE PRIOR ART

Heretofore, time of flight mass spectrometers have employed a first gate between the ion source and the drift tube and a second gate operatively associated with the detector at the output of the drift tube. These gates were driven by the same modulation function which was a pseudo random pulse sequence with the second gate signal being variably delayed relative to the first gate signal. The variable delay was then swept over a range to obtain an output mass spectrum in the time domain, i.e., a conventional time of flight mass spectrum. The advantage of utilizing the two gates driven with the same modulation function is that the duty cycle, i.e., the number of ions passing between the source and the detector and signal-to-noise ratio are greatly increased over the more conventional time of flight mass spectrometer in which ions from the source were gated with a short pulse and their arrival time measured at the detector for deriving a mass spectrum of the sample under analysis. The more conventional time of flight mass spectrometer is disclosed in U.S. Pat. No. 4,458,149 issued Jul. 3 1984.

The pseudo random gated time of flight mass spectrometer is disclosed in an article entitled: "A Miniature Time of Flight Mass Spectrometer" appearing in Vacuum, volume 21, #10, pgs. 461-464 published by Pergamon Press in 1971.

While the pseudo random modulated time of flight mass spectrometer provides increased duty cycle and thus signal-to-noise as contrasted with the more conventional time of flight mass spectrometer, the associated random pulse generator, variable delay, and associated amplifiers are relatively sophisticated and costly due to requirements for relatively broad band phase linear performance.

It would be desirable to provide an improved time of flight spectrometer which could provide the increased signal-to-noise ratio and duty cycle while utilizing less costly associated electronics and signal processing equipment.

SUMMARY OF THE PRESENT INVENTION

The principal object of the present invention is the provision of an improved time of flight mass spectrometer employing Fourier transform signal processing.

In one feature of the present invention, the flow of ions from the ion source through the drift tube region to the detector is modulated at a certain modulation frequency which is swept and the output is detected as a function of the modulation frequency to obtain an ion mass interferogram output which is thence Fourier transformed into the time domain to obtain a time of flight mass spectrum of the substance under analysis, whereby improved signal-to-noise is obtained with a relatively high duty cycle while utilizing less costly signal measurement electronics.

In another feature of the present invention, the flow of ions from the drift region into the detector is modulated at the same modulation frequency at which the flow of ions from the source into the drift region is modulated.

In another feature of the present invention, the flow of ions from the source into the drift region and the flow of ions from the drift region into the detector are both modulated simultaneously with the same modulation frequency, thereby simplifying the ion flow modulation scheme.

In another feature of the present invention, the flow of ions from the source into the drift region is modulated with a sinusoidal function at the modulation frequency.

Other features and advantages of the present invention will become apparent upon a perusal of the following specification taken in connection with the accompanying drawings wherein:

BRIEF DESCRIPTION OF THE DRAWINGS

FIG. 1 is a schematic diagram, partly in block diagram form, of a Fourier transform mass spectrometer incorporating features of the present invention;

FIG. 2 is a plot of various waveforms encountered in the system of FIG. 1;

FIG. 3 is an interferogram output derived at the output of the detector in the system of FIG. 1; and, FIG. 4 is a time of flight mass spectrum of a sample of toluene as derived from the output of the spectrometer of FIG. 1.

DESCRIPTION OF THE PREFERRED EMBODIMENTS

Referring now to FIG. 1, there is shown a Fourier transform time of flight mass spectrometer 11 incorporating features of present invention. The spectrometer 11 includes an evacuable envelope 12 containing certain elements of the spectrometer. The envelope 12 and its internal elements are substantially the same as those of the conventional time of flight spectrometer having a one meter length flight tube, for example, the model 2001 time of flight mass spectrometer commercially available from CVC Products of Rochester, N.Y.

Briefly, the evacuable envelope 12 includes an ion source 13, at one end, for ionizing a substance under analysis admitted into the envelope 12 by means of tubulation 14. Operatively associated with the ion source 13 are draw-out and acceleration grids 15 and 16, respectively, for drawing out the ions from the ion source 13 and accelerating them into a field-free drift region 17 to an ion detector 18 at the far end of the envelope 12. Electrostatic steering plates 19 of conventional design are disposed at the entrance to the drift region 17 for steering the ions into and through the drift region to the detector 18.

The ion source 13 includes a thermionic emitting filament 21 for directing a stream of electrons across the ion source to an electron collector 22. The electron current in the electron beam serves to ionize the gaseous species under analysis. A backplate 23 of the ion source 13 serves as a repeller electrode and in cooperation with the first accelerating or draw-out grid 15 serves to draw the ionized gaseous constituents into the accelerating grid assembly 16 and thence through the steering plates 19 into the drift region 17.

The ion detector 18 includes an electron multiplier section 25, which multiplies the electron secondary emission generated by impingement of an ion on a collector electrode portion 26 of the electron multiplier 25. The multiplied electron current is collected on an anode 27 of the detector 18 and a detector electrode 28 is provided for gating on and off the electron current to the anode 27.

In the fourier transform mode of operation, the spectrometer 11 includes a frequency generator 31 which produces a sinusoidal output signal at a given frequency. This output is amplified in an rf amplifier 32 and thence fed via d.c. isolating capacitors 33 and 34 to the draw-out electrode 15 and detector gate 28, respectively. Thus, the ion source 13 and detector 18 are both gated simultaneously with the same modulation function, i.e., sinusoidal waveform produced from the output of the frequency generator 31. D.C. biasing voltages are applied to the respective draw-out grid 15 and detector gate electrode 28 via d.c. voltage supplies 35 and 36, respectively. In a typical example, the frequency generator 31 comprises a model 200 frequency synthesizer commercially available from Programmed Test Source Inc. of Littletown, Ma. Its output frequency is tunable from 1 to 200 MHz.

The output frequency of the frequency generator 31 is stepped or tuned over a desired tuning range by means of a microprocessor 38, such as an Apple IIe computer, which is interfaced to the frequency generator 31 by means of a general purpose interface circuit-board 39 such as a model 7490A commercially available from California Computer Systems of Sunnyvale, Calif. The microprocessor 38 is operated by means of a conventional keyboard 41.

The output signal received on anode 27 of the detector 18 is fed to one input of a fourier transform computer 42 such as a model 1080 instrument computer commercially available from Nicolet Instrument Corp. of Madison, Wis. The frequency output of the frequency generator 31 is correlated with the respective channels of the fourier transform computer 42 by means of an output derived from the microprocessor 38 and fed to the fourier transform computer 42 via the interface board 39.

The output signal of the detector 18 is an ion interferogram signal of the type shown in FIG. 3 in which the detected ion current is obtained as a function of the modulation frequency applied to gates 15 and 28. This interferogram output signal is fourier transformed from the frequency domain to the time domain utilizing the conventional fourier transform properties of the computer 42 to obtain a conventional time of flight mass spectrum which is thence recorded on the recorder 43.

The recorded output is as shown in FIG. 4 where the intensity of various mass lines are shown as a function of flight time. The spectrum depicted in FIG. 4 is that obtained from a sample of toluene being analyzed. The interferogram of FIG. 3 represents 2,048 data points. This interferogram was taken between 1 to 17 MHz. The lower frequency was determined by the range of the frequency generator 31. The upper frequency is the limit of useful information. For this data set, the frequency generator 31 was stepped at 8 KHz per data point and was held at each frequency for one second for a total scan time of 30 minutes. More rapid scans are possible with a more rapidly swept frequency generator 31.

FIG. 4 shows the intensity spectrum of the fourier transform of the interferogram illustrated in FIG. 3. Only the first 250 data points of the transform are shown and this represents the time domain time of flight mass spectrum for the sample under analysis, namely, toluene.

THEORY OF OPERATION

In the fourier transform time of flight mass spectrometer the mechanism is:

1. Modulate or gate the ions into the flight tube 17 and the signal reaching the anode 27 of the detector 18 simultaneously with a periodic function. Typically, the modulation function or waveform is a sine wave, although any periodic function is acceptable.
2. Sweep the frequency of the modulation function while keeping its relative shape constant. The width of the frequency sweep determines the resolution of the transformed spectrum.
3. Obtain an output signal as a function of applied modulation frequency. This output will be referred to as an ion interferogram.
4. Calculate the fourier transform (magnitudes in this case), which gives the time domain spectrum.

In the fourier transform time of flight mass spectrometer, a whole family of flight times are selected for each applied frequency and the distribution of flight times detected is varied by changing the modulation frequency. The distribution of flight times that are selected by a modulation sequence can be represented by the correlation of the source transmission function and the signal sampling function.

$$\epsilon(t_f) = T^{-1} \int_{-\frac{1}{2}T}^{\frac{1}{2}T} e(t - t_f)f(t)dt \qquad \text{Eq. (1)}$$

where t is real time, $t_f$ is ion flight time, e(t) is the source transmission modulation function, f(t) if the signal sampling function, T is the integration time of the electronics (essentially infinity here).

A value of $\epsilon(t_f)$ for a particular set of modulation conditions represents the fraction of ions of flight time $t_f$ that reach the anode 27 and get measured. If a sample having TOF spectrum $m(t_f)$ is measured, the detected signal is $$S = \int m(t_f)\epsilon(t_f) \, dt_f \qquad \text{Eq. (2)}$$

That is, the intrinsic intensity of ions of flight time $t_f$, $m(t_f)$, is multiplied by the fraction of those ions that get detected, $\epsilon(t_f)$, and that product is summed over all flight times. S and $\epsilon(t_f)$ are functions of the particular modulation sequence through Equation (1).

For FT mode operation, e(t) equals f(t) and will be represented as a binary square wave. (See FIG. 2a). Although experimentally the draw-out grid 15 and deflection plate 28 were driven with a sinusoidal function, the ion and electron density generated may be more like a square wave. Furthermore, using a square wave modulation function points out how overtones in the transformed spectrum arise from non-sinusoidal modulation. In addition, a binary square wave is used because gating the signal on and off is easy to visualize. FIG. (2a) shows the form of e(t) used.

The gate correlation function, $\epsilon(t_f,v)$ is illustrated in FIG. (2b) as a function of flight time for a particular modulation frequency. Equation (1) states that the gate correlation function is the correlation of the source transmission and signal sampling functions. Therefore, FIG. (2b) is a triangle wave—the autocorrelation function of FIG. (2a). $\epsilon(t_f,v)$ illustrates the relative efficiency of detection of ions of flight time $t_f$ for a modulation frequency $v$. Ions whose flight times are integral values of the reciprocal of the applied modulation frequency are detected with maximum efficiency. Ions with flight times equal to half integral values of the reciprocal of the modulation frequency are not detected at all; and ions with flight times intermediate to integral and half integral values of the frequency are detected with intermediate efficiency.

The interferogram output signal is obtained as a function of frequency. The value of the output waveform is given by $$S(v) = \int m(t_f)\epsilon(t_f, v) \, dt_f \qquad \text{Eq. (3)}$$

where the integration is over all flight times. The interferogram output signal, $S(v)$ and the TOF spectrum, $m(t_f)$, are $\epsilon$—transforms of each other, and $\epsilon(t_f,v)$ is the kernel of the transform. It is the periodic and essentially cosinusoidal nature of $\epsilon(t_f, v)$ which will justify Fourier transformation. In fact, if a sinusoidal modulation function, had been used rather than the square wave, $\epsilon(t_f,v)$ would be $\cos 2\pi v t$ and $S(v)$ would be the cosine transform of $m(t_f)$.

It is helpful to consider the shape of the interferogram if the TOF spectrum consists of a single component of a single flight time. This single ion interferogram is illustrated in FIG. (2c). When the applied frequency is equal to the reciprocal of the ion flight time, the detector signal is a maximum. When the applied frequency is equal to a half integral value of the ion flight time, the detector signal is zero. FIG. (2b and c) illustrate that $\epsilon(t_f,v)$ is a periodic function of two variables.

The proper way to recover $m(t_f)$ from $S(v)$ would be to perform an inverse $\epsilon$-transform. However, since the exact shape of $\epsilon(t_f,v)$ is not known, but its shape is periodic and since fast Fourier transform routines are widespread and efficient, $m(t_f)$ is recovered through the Fourier transform. Taking the form of $\epsilon(t_f,v)$ to be the triangle wave illustrated in FIG. (2b), it is expanded in terms of its Fourier series. The integral of Eqn. (2) becomes:

$$S(v) = \frac{1}{4} \int_0^m m(t_f) dt_f + \qquad \text{Eq. (4)}$$

$$\frac{2}{\pi^2} \sum_{n=1,3,5\ldots} \frac{1}{n^2} \int_0^\infty m(t_f)\cos 2\pi \eta v t_f dt_f$$

$$= \frac{1}{4} I_0 + \frac{1}{\pi^2} \sum_{n=1,3,5\ldots} \frac{1}{n^3} F_c m\left(\frac{t_f}{n}\right) \qquad \text{Eq. (5)}$$

where $I_0$ is the unmodulated ion current and $F_c$ is the consine transform. Thus, $S(v)$ is the cosine transform of the TOF spectrum plus a DC offset plus some odd overtones. The DC offset comes from the DC offset of the signal, there being no negative ion current. The odd overtones appear due to the non-sinusoidal nature of the modulation function.

An additional complication arises when doing rapid scans. If the modulation frequency changes on the time scale of the ion flight time, then the sampling frequency is not the same frequency as the arriving ion signal. The sampling function is e(t), but the ion signal is $e(t-t_f)$. The gate correlation is now:

$$\epsilon(t_f,t) = \frac{1}{T} \int_{t-\frac{T}{2}}^{t+\frac{T}{2}} e(t-t_f)e(t)dt \qquad \text{Eq. (6)}$$

Using a linear frequency sweep modulation function, $\sin 2\pi(v_0+Rt)t$, where $v_0$ is the start frequency of the scan, R is the scan rate in Hz s$^{-1}$, then Eqn. (6) becomes:

$$\epsilon(t_f,t) = \frac{1}{T} \int_{t-\frac{T}{2}}^{t+\frac{T}{2}} \frac{1}{2}[\cos 2\pi(2v_0 t - v_0 t_f + Rt^2 - \qquad \text{Eq. (7)}$$

$$Rtt_f + \tfrac{1}{2}Rt_f^2 + \cos 2\pi(v_0 t_f + Rtt_f - \tfrac{1}{2}Rt_f^2)]dt$$

Eqn. 7 represents the sum and difference frequencies of the product in Eqn. (6). The integral over the time constant of the electronics will be utilized to eliminate the high frequency sum term, and the low frequency term is passed unchanged. The difference term, the measured signal is then, $$\epsilon(t_f,t)=\cos(v_0 t_f + Rtt_f - \tfrac{1}{2}Rt_f^2) \qquad \text{Eq. (8)}$$

For an ion of drift time $t_f$ and for a scan rate of R, the excursions of the interferogram appear at a frequency $Rt_f$. Recognizing that $v=v_0+Rt$, $\epsilon$ is expressed in terms of the applied frequency as $$\epsilon(t_f,v)=\cos 2\pi(v-\tfrac{1}{2}Rt_f)t_f \qquad \text{Eq. (9)}$$

The recorded interferogram as a function of frequency for the rapid scan case has a flight time dependent phase shift of 0.5 $Rt_f$. The period of the interferogram is still $1/t_f$. For rapid scan conditions, the magnitude spectra are unaffected by the scan rate. For this reason the magnitude spectra of the interferograms is calculated.

Operation of the TOF MS in the Fourier mode cannot improve on the fundamental resolution of the instrument. Ultimate resolution is dictated by the physics governing the TOF separations process and by the configuration of the instrument. Peak broadening due to instrumental limitations in the time domain can be thought of as a pure TOF spectrum—a series of $\gamma$ functions representing a spectrum of infinite resolution—convoluted with an instrumental response function. In the Fourier domain, this relationship is expressed as a multiplication of the interferogram by a frequency transfer function. The frequency transfer function and the instrumental response function are a Fourier transform pair. This frequency transfer function manifests itself in the measured interferogram as an envelope which attenuates the intensity of the interferogram at high frequencies. The time resolution of the transformed spectrum is roughly proportional of the frequency bandwidth of the interferogram envelope function.

Sensitivity, or S/N is related to the amount of time that the source is broadcasting to the detector, or in other words, the duty cycle; while the resolution is proportional to the modulation bandwidth. In conventional (time domain) operation of TOF, bandwidth is achieved by modulating the source with a very narrow function, the narrower the pulse width, the higher the bandwidth of the modulation and the higher the resolution. This bandwidth is achieved at the expense of the duty cycle of the instrument, though. In FT TOF, frequency bandwidth is achieved by measuring the interferogram over a large range of modulation frequencies while maintaining a 25% duty cycle throughout.

Although, as thus far described, the mathematical transform utilized has been the Fourier transform, for transforming the frequency domain interferogram into the time domain spectrum, other mathematical transformations may be used. More particularly, some applicable conventional mathematical techniques are the Walsh transform or the LaPlace transform.

The advantage of the Fourier transform time of flight mass spectrometer of the present invention is that it results in higher signal strengths compared to conventional time of flight operation and this is translatable to increased sensitivity and decreased scan time for the time of flight mass spectrometer.

What is claimed is:

1. In a method for operating a time of flight mass spectrometer of the type having an evacuable envelope containing a source of ions for ionizing a substance under analysis, means for extracting and accelerating the ions to produce a flow of ions from the source into an ion drift region and thence into a detector for detecting the ions which have passed through the drift region, the steps of:

modulating the flow of ions from the ion source and through the evacuated drift region at subatmospheric pressure to the detector at a certain modulation frequency;

changing the frequency of the modulation frequency;

detecting the flow of ions into the detector as a function of the modulation frequency to obtain an ion mass interferogram output consisting of detected ion current as a function of modulation frequency in the frequency domain; and transforming the ion mass interferogram output in the frequency domain into the time domain to obtain a time domain mass spectrum output of the substance under analysis comprising detected ion current as a function of flight time through the drift region to the detector.

2. The method of claim 1 including the step of modulating the flow of ions from the drift region into the detector at the same modulation frequency at which the flow of ions from said ion source into the drift region is modulated.

3. The method of claim 2 wherein flow of ions from the ions source into the drift region and flow of ions from the drift region into the detector are both modulated simultaneously with the same modulation frequency.

4. The method of claim 1 wherein the flow of ions from the source into the ion drift region is modulated with a sinusoidal function at the modulation frequency.

5. In a time of flight mass spectrometer;

evacuable envelope means for containing elements of the spectrometer at sub-atmospheric pressure;

ion source means for disposition within said envelope means for ionizing a substance under analysis;

drift tube means for disposition within said evacuable envelope means for providing a drift region at sub-atmospheric pressure through which ions from said source means are allowed to drift;

ion extracting and accelerating means for disposition within said evacuable envelope means between said ion source means and said drift tube means for extracting ions from said ion source means and accelerating said ions into a flow into said drift tube means;

detector means for disposition within said envelope means for receiving and detecting the flow of ions through said drift region of said drift tube means to said detector means;

first modulating means for modulating the flow of ions from said ion source means into said drift tube means at a modulation frequency;

frequency changing means for changing the modulation frequency of said first modulating means at which the flow of ions from said ion source means into said drift tube means and thence to said detector means is modulated to produce an ion mass interferogram output of said detector in which the detected ion flow is obtained as a function of modulation frequency; and transforming means operable on said mass interferogram output for transforming said ion mass interferogram output into a time domain ion mass spectrum output of the substance under analysis and comprising detected ion flow as a function of flight time through the drift tube means to said detector means.

6. The spectrometer of claim 5 including;

second modulating means for modulating the detection of the flow of ions into said detector means at the same modulation frequency at which the flow of ions from said ion source means into the drift tube means is modulated.

7. The spectrometer of claim 6 including;

means for modulating said first and second modulating means simultaneously at the same modulation frequency.

8. The spectrometer of claim 5 wherein said first modulating means is modulated by a sinusoidal function of time.

* * * * *